(12) United States Patent
Tuschl et al.

(10) Patent No.: US 8,470,797 B2
(45) Date of Patent: Jun. 25, 2013

(54) INDUCIBLE SMALL RNA EXPRESSION CONSTRUCTS FOR TARGETED GENE SILENCING

(75) Inventors: Thomas Tuschl, New York, NY (US); Tilmann Achsel, Grottaferrato (IT); Reinhard Luehrmann, Marburg-Michelbach (DE); Jutta Myer, Roosevelt Island, NY (US)

(73) Assignee: Max-Planck-Gesellschaft zur Foerderung der Wissenschaften e.V., Munich (DE)

( * ) Notice: Subject to any disclaimer, the term of this patent is extended or adjusted under 35 U.S.C. 154(b) by 0 days.

(21) Appl. No.: 13/438,170

(22) Filed: Apr. 3, 2012

(65) Prior Publication Data

US 2012/0255045 A1    Oct. 4, 2012

Related U.S. Application Data (62) Division of application No. 10/542,592, filed as application No. PCT/EP2004/000265 on Jan. 15, 2004, now Pat. No. 8,198,077.

(30) Foreign Application Priority Data

Jan. 17, 2003 (EP) .................................... 03001058

(51) Int. Cl.
*C12N 15/11* (2006.01)
(52) U.S. Cl.
USPC ........................................................ 514/44 A
(58) Field of Classification Search
USPC ........................................................ 514/44 A
See application file for complete search history.

(56) References Cited

U.S. PATENT DOCUMENTS

| | | | |
|---|---|---|---|
| 5,891,718 | A | 4/1999 | Hobart et al. |
| 6,506,559 | B1 | 1/2003 | Fire et al. |
| 7,094,876 | B2 | 8/2006 | Bejanin et al. |
| 7,176,304 | B2 | 2/2007 | McSwiggen et al. |
| 7,195,916 | B2 | 3/2007 | Qin et al. |
| 2004/0040052 | A1 | 2/2004 | Radcliffe et al. |
| 2005/0071893 | A1 | 3/2005 | Seibler et al. |

FOREIGN PATENT DOCUMENTS

WO   WO 2004/056964   7/2004

OTHER PUBLICATIONS

Czauderna, F. et al., "Inducible SHRNA Expression for Application in a Prostate Cancer Mouse Model", Nucleic Acids Research, Nov. 2003, p. e127, vol. 31(21), XP002291076.

Luukkonen, B., et al., "Construction of an In Vivo-Regulated U6 SNRNA Transcription Unit as a Tool to Study U6 Function", RNA, Feb. 1998, pp. 231-238, vol. 4(2), XP002291073.

Matsukura, S. et al., "Establishment of Conditional Vectors for Hairpin SIRNA Knockdowns", Nucleic Acids Research, Aug. 2003, p. e77, vol. 31(15), XP002291075.

Ohkawa, J. et al., "Control of the Functional Activity of an Antisense RNA by a Tetracycline-Responsive Derivative of the Human U6 SNRNA Promotor", Human Gene Therapy, Mar. 2000, pp. 577-585, vol. 11(4), XP000926522.

Xia X., et al., "An Enhanced U6 Promoter for Synthesis of Short Hairpin RNA", Nucleic Acids Research, Sep. 2003, p. e100, vol. 31(17), XP002291074.

European Search Report dated Mar. 3, 2011 in Application No. 10179492.3-2403.

*Primary Examiner* — Brian Whiteman
(74) *Attorney, Agent, or Firm* — Rothwell, Figg, Ernst & Manbeck, P.C.

(57) ABSTRACT

The invention relates to vectors for the inducible expression of RNA molecules in eukaryotic, particularly mammalian cells and transgenic animals.

8 Claims, 6 Drawing Sheets

Fig 1

```
H1 promoter  5'AATATTTGCATGTCGCTATGTGTTCTGGGAAATCACCATAAACGTGAAATGTCTTTGGATTTG
             GGAATCTTATAAGTTCTGTATGAGACCACTCGAATTC
GL2 hairpin  5' ATTTCGAAGTATTCCGCGTACGTTTCGACGTACGCGGAATACTTCGAAA
terminator   5' TTTTTTCTCGAGCTTCCCTCGGGAAGCTCTCCATATTTTTTGGATCC
```

Fig 2

```
H1     PSE ... TGTCTTTGGATTTGGGAATCTTATAAGTTCTGTATGAGACCACTCGAATTC ... GL2 ...
tetO1  PSE ... ▓▓▓▓▓▓▓▓▓▓▓▓▓▓▓▓▓▓▓▓CTTATAAGTTCTGTATGAGACCACTCGAATTC ... GL2 ...
tetO2  PSE ... TGTCTTTGGATTTGGGAATCTTATAA▓▓▓▓▓▓▓▓▓▓▓▓▓▓▓▓▓▓▓▓GAAATTC ... GL2 ...
tetO3  PSE ... TGTCTTTGGATTTGGGAATCTTATAAGT▓▓▓▓▓▓▓▓▓▓▓▓▓▓▓▓▓▓▓▓ATTC ... GL2 ...
tetO4  PSE ... ▓▓▓▓▓▓▓▓▓▓▓▓▓▓▓▓▓▓▓▓CTTATAAGT▓▓▓▓▓▓▓▓▓▓▓▓▓▓▓▓▓▓▓▓ATTC ... GL2
(green: TATA-box; red: tetR-binding site).
```

```
LOCUS
DEFINITION  pH1-TetO4, dereived from pBluescript SK(-)
SOURCE      T. Achsel, J. Meyer, T. Tuschl, MPI f. biophys. Chem, Goettingen,
Germany
  ORGANISM  unknown
FEATURES             Location/Qualifiers
     misc_feature    749..752
                     /note=""
                     /standard_name="TATA-box"
     misc_feature    order(728..746,756..774)
                     /note=""
                     /standard_name="tetO2 site"
     misc_feature    679..778
                     /note=""
                     /standard_name="H1 promoter"
     misc_feature    order(779..826,826..828)
                     /note=""
                     /standard_name="GL2 hairpin RNA"
     misc_feature    668..673
                     /note=""
                     /standard_name="inactivated XhoI site"
     terminator      828..868
                     /note=""
                     /standard_name="terminator"
BASE COUNT      749 a    784 c    753 g    822 t
ORIGIN
        1 CACCTGACGC GCCCTGTAGC GGCGCATTAA GCGCGGCGGG TGTGGTGGTT ACGCGCAGCG
       61 TGACCGCTAC ACTTGCCAGC GCCCTAGCGC CCGCTCCTTT CGCTTTCTTC CCTTCCTTTC
      121 TCGCCACGTT CGCCGGCTTT CCCCGTCAAG CTCTAAATCG GGGGCTCCCT TTAGGGTTCC
      181 GATTTAGTGC TTTACGGCAC CTCGACCCCA AAAAACTTGA TTAGGGTGAT GGTTCACGTA
      241 GTGGGCCATC GCCCTGATAG ACGGTTTTTC GCCCTTTGAC GTTGGAGTCC ACGTTCTTTA
      301 ATAGTGGACT CTTGTTCCAA ACTGGAACAA CACTCAACCC TATCTCGGTC TATTCTTTTG
      361 ATTTATAAGG GATTTTGCCG ATTTCGGCCT ATTGGTTAAA AAATGAGCTG ATTTAACAAA
      421 AATTTAACGC GAATTTTAAC AAAATATTAA CGCTTACAAT TTCCATTCGC CATTCAGGCT
      481 GCGCAACTGT TGGGAAGGGC GATCGGTGCG GGCCTCTTCG CTATTACGCC AGCTGGCGAA
      541 AGGGGGATGT GCTGCAAGGC GATTAAGTTG GGTAACGCCA GGGTTTCCC AGTCACGACG
      601 TTGTAAAACG ACGGCCAGTG AATTGTAATA CGACTCACTA TAGGGCGAAT TGGGTACCGG
      661 GCCCCCCCTC GAAGATCTAA TATTTGCATG TCGCTATGTG TTCTGGGAAA TCACCATAAA
      721 CGTGAAATCC CTATCAGTGA TAGAGTTATA TAAGTTCCCT ATCAGTGATA GAGAATTCAT
      781 TTCGAAGTAT TCCGCGTACG TTTCGACGTA CGCGGAATAC TTCGAAATTT TTTCTCGAGC
      841 TTCCTTCGGG AAGCTCTCCA TATTTTTTGG ATCCACTAGT TCTAGAGCGG CCGCCACCGC
      901 GGTGGAGCTC CAGCTTTTGT TCCCTTTAGT GAGGGTTAAT TTCGAGCTTG GCGTAATCAT
      961 GGTCATAGCT GTTTCCTGTG TGAAATTGTT ATCCGCTCAC AATTCCACAC AACATACGAG
     1021 CCGGAAGCAT AAAGTGTAAA GCCTGGGGTG CCTAATGAGT GAGCTAACTC ACATTAATTG
     1081 CGTTGCGCTC ACTGCCCGCT TTCCAGTCGG GAAACCTGTC GTGCCAGCTG CATTAATGAA
     1141 TCGGCCAACG CGCGGGGAGA GGCGGTTTGC GTATTGGGCG CTCTTCCGCT TCCTCGCTCA
     1201 CTGACTCGCT GCGCTCGGTC GTTCGGCTGC GGCGAGCGGT ATCAGCTCAC TCAAAGGCGG
     1261 TAATACGGTT ATCCACAGAA TCAGGGGATA ACGCAGGAAA GAACATGTGA GCAAAAGGCC
     1321 AGCAAAAGGC CAGGAACCGT AAAAAGGCCG CGTTGCTGGC GTTTTTCCAT AGGCTCCGCC
     1381 CCCCTGACGA GCATCACAAA AATCGACGCT CAAGTCAGAG GTGGCGAAAC CCGACAGGAC
     1441 TATAAAGATA CCAGGCGTTT CCCCCTGGAA GCTCCCTCGT GCGCTCTCCT GTTCCGACCC
     1501 TGCCGCTTAC CGGATACCTG TCCGCCTTTC TCCCTTCGGG AAGCGTGGCG CTTTCTCATA
     1561 GCTCACGCTG TAGGTATCTC AGTTCGGTGT AGGTCGTTCG CTCCAAGCTG GGCTGTGTGC
     1621 ACGAACCCCC CGTTCAGCCC GACCGCTGCG CCTTATCCGG TAACTATCGT CTTGAGTCCA
     1681 ACCCGGTAAG ACACGACTTA TCGCCACTGG CAGCAGCCAC TGGTAACAGG ATTAGCAGAG
     1741 CGAGGTATGT AGGCGGTGCT ACAGAGTTCT TGAAGTGGTG GCCTAACTAC GGCTACACTA
     1801 GAAGGACAGT ATTTGGTATC TGCGCTCTGC TGAAGCCAGT TACCTTCGGA AAAAGAGTTG
     1861 GTAGCTCTTG ATCCGGCAAA CAAACCACCG CTGGTAGCGG TGGTTTTTTT GTTTGCAAGC
     1921 AGCAGATTAC GCGCAGAAAA AAAGGATCTC AAGAAGATCC TTTGATCTTT TCTACGGGGT
     1981 CTGACGCTCA GTGGAACGAA AACTCACGTT AAGGGATTTT GGTCATGAGA TTATCAAAAA
     2041 GGATCTTCAC CTAGATCCTT TTAAATTAAA AATGAAGTTT TAAATCAATC TAAAGTATAT
     2101 ATGAGTAAAC TTGGTCTGAC AGTTACCAAT GCTTAATCAG TGAGGCACCT ATCTCAGCGA
     2161 TCTGTCTATT TCGTTCATCC ATAGTTGCCT GACTCCCCGT CGTGTAGATA ACTACGATAC
     2221 GGGAGGGCTT ACCATCTGGC CCCAGTGCTG CAATGATACC GCGAGACCCA CGCTCACCGG
     2281 CTCCAGATTT ATCAGCAATA AACCAGCCAG CCGGAAGGGC CGAGCGCAGA AGTGGTCCTG
     2341 CAACTTTATC CGCCTCCATC CAGTCTATTA ATTGTTGCCG GGAAGCTAGA GTAAGTAGTT
     2401 CGCCAGTTAA TAGTTTGCGC AACGTTGTTG CCATTGCTAC AGGCATCGTG GTGTCACGCT
```

Fig 5 continued

```
2461 CGTCGTTTGG TATGGCTTCA TTCAGCTCCG GTTCCCAACG ATCAAGGCGA GTTACATGAT
2521 CCCCCATGTT GTGCAAAAAA GCGGTTAGCT CCTTCGGTCC TCCGATCGTT GTCAGAAGTA
2581 AGTTGGCCGC AGTGTTATCA CTCATGGTTA TGGCAGCACT GCATAATTCT CTTACTGTCA
2641 TGCCATCCGT AAGATGCTTT TCTGTGACTG GTGAGTACTC AACCAAGTCA TTCTGAGAAT
2701 AGTGTATGCG GCGACCGAGT TGCTCTTGCC CGGCGTCAAT ACGGGATAAT ACCGCGCCAC
2761 ATAGCAGAAC TTTAAAAGTG CTCATCATTG GAAAACGTTC TTCGGGGCGA AAACTCTCAA
2821 GGATCTTACC GCTGTTGAGA TCCAGTTCGA TGTAACCCAC TCGTGCACCC AACTGATCTT
2881 CAGCATCTTT TACTTTCACC AGCGTTTCTG GGTGAGCAAA AACAGGAAGG CAAAATGCCG
2941 CAAAAAAGGG AATAAGGGCG ACACGGAAAT GTTGAATACT CATACTCTTC CTTTTTCAAT
3001 ATTATTGAAG CATTTATCAG GGTTATTGTC TCATGAGCGG ATACATATTT GAATGTATTT
3061 AGAAAAATAA ACAAATAGGG GTTCCGCGCA CATTTCCCCG AAAAGTGC
```

INDUCIBLE SMALL RNA EXPRESSION CONSTRUCTS FOR TARGETED GENE SILENCING

CROSS REFERENCE TO RELATED APPLICATION

This application is a divisional of U.S. Ser. No. 10/542,592 filed Oct. 18, 2005 which is a 35 U.S.C. §371 National Phase Entry Application from PCT/EP2004/000265, filed Jan. 15, 2004, which claims the benefit of European Patent Application No. 03001058.1 filed on Jan. 17, 2003, the disclosures of which are incorporated herein in its entirety by reference.

DESCRIPTION

The invention relates to vectors for the inducible expression of RNA molecules in eukaryotic, particularly mammalian cells and organisms.

Small double-stranded RNAs of approximately 20 to 30 base pairs have been shown to sequence-specifically direct mRNA degradation in mammalian cells (McManus and Sharp 2002). These small interfering RNAs (siRNAs) are preferentially 21 nucleotide (nt) long and paired such that they have a 19 base pair stem and 2-nt 3'-overhanging ends (Elbashir et al. 2001b; Elbashir et al. 2001a; Elbashir et al. 2001c; Elbashir et al. 2002). Such siRNA duplexes can be delivered into mammalian cells by microinjection, transfection or electroporation and may become a new class of therapeutic agents directed against genes that have been associated with pathogenesis, such as viral genes, by destroying their mRNAs and thereby preventing their expression (Paddison and Hannon 2002; Tuschl and Borkhardt 2002). Double-stranded RNA longer than 30 base pairs can activate the interferon response causing unspecific translational arrest and apoptosis; these effects have not been observed with shorter dsRNAs (Bitko and Bark 2001; Elbashir et al. 2001b).

More recently a new class of genes was discovered that encode short dsRNA hairpin loops of about 25 to 30 basepairs in length that are processed to 21 to 23 nucleotide small RNAs (Lagos-Quintana et al. 2001; Lau et al. 2001; Lee and Ambros 2001; Lagos-Quintana et al. 2002). This class was termed microRNAs. microRNAs function in the same pathway than siRNAs by associating with Argonaute proteins that are required for guiding target mRNA recognition (Hutvagner and Zamore 2002; Martinez et al. 2002; Mourelatos et al. 2002). miRNAs cleave complementary target mRNAs in plants (Llave et al. 2002; Rhoades et al. 2002) but appear to repress mRNA translation rather than mRNA cleavage in animals (Hutvagner and Zamore 2002).

For gene targeting experiments, siRNAs were until recently introduced into cells via classic gene transfer methods such as liposome-mediated transfection, electroporation, or microinjection, which required chemical or enzymatic synthesis of siRNAs prior to its application, but siRNAs can also be generated intracellularily by expression of siRNAs from plasmid DNA or retroviral, lentiviral or adenoviral constructs (Barton and Medzhitov 2002; Brummelkamp et al. 2002a; Brummelkamp et al. 2002b; Devroe and Silver 2002; McManus et al. 2002; Miyagishi and Taira 2002; Xia et al. 2002; Zeng et al. 2002). Intracellular transcription of small RNA molecules is possible by cloning the siRNA templates into RNA polymerase III (pol III) transcription units, which normally encode the small nuclear RNA U6 or the human RNase P RNA H1. Two approaches have been developed for expressing siRNAs: (1) The sense and antisense strands constituting the siRNA duplex are transcribed by individual promoters (Lee et al. 2002; Miyagishi and Taira 2002) or (2) siRNAs are expressed as fold-back stem-loop structures that give rise to siRNAs after intracellular processing (Brummelkamp et al. 2002b; Paul et al. 2002). The endogenous expression of siRNAs from introduced DNA templates is thought to overcome some limitations of exogenous siRNA delivery, in particular the transient loss-of-phenotype.

U6 and H1 RNA promoters are members of the type III of pol III promoters (Paule and White 2000). These promoters are unusual in that almost all their elements, with exception of the first transcribed nucleotide (+1 position), are located upstream of the transcribed region so that almost any inserted sequence shorter than 400 nt can be transcribed. They are therefore ideally suited for expression of the approximately 21-nt siRNAs or the approximately 50-nt RNA stem-loops. The U6 promoter and the H1 promoter are different in size but contain the same conserved sequence elements or protein binding sites (Myslinski et al. 2001). The +1 nucleotide of the U6-like promoters is always guanosine, and always adenosine for H1. Interestingly, changing the +1 adenosine to U, C or G within H1 expressed stem-loop sequences did not seem to affect gene silencing, therefore suggesting that H1 promoters may be more flexible than U6 promoters for +1 sequence changes or may be able to initiate transcription at the first downstream purine nucleotide encoded by the template DNA (Brummelkamp et al. 2002b). RNA transcription is terminated when pol III encounters a run of 4 or 5 thymidines after incorporation of several uridine residues (Myslinski et al. 2001).

For practical applications, however, the considerable extra time involved in preparing and amplifying siRNA expression vectors and the transfection efficiency of plasmids relative to siRNAs must also be considered. Furthermore, targeting of essential genes causes arrest in cell growth or cell death within one to three days after delivery of siRNAs, thus making long-term silencing unnecessary if not impossible; the development of inducible siRNA expression systems may however provide an interesting alternative in such cases (Ohkawa and Taira 2000). However, when targeting non-essential proteins, stable knockdown cells may be of great value when studying inducible processes such as UV/irradiation damage response, host-pathogen interactions, or cell differentiation. In order to overcome the limitation of presently available targeting vectors we have explored the possibility of inserting regulatory protein binding sequences into the promoter region of pol III promoters.

A first aspect of the present invention is a recombinant vector for the inducible expression of a single-stranded or double-stranded RNA molecule in a eukaryotic, particularly mammalian, cell comprising at least one sequence coding for the RNA molecule operatively linked to an expression control sequence comprising a polymerase III promoter and at least one regulatory protein binding site and optionally a transcription terminator. The polymerase III promoter and the regulatory protein binding site are located 5' to the coding sequence and the terminator is located 3' to the coding sequence.

The vector may be any vector which is suitable for the transfection of eukaryotic cells, e.g. a DNA or an RNA vector. The vector may be a plasmid, for example a linear or a circular plasmid, a cosmid, a viral vector, for example, an adenovirus, retrovirus, adeno-associated virus, vaccina virus, lentivirus or an artificial chromosome. The vector may be an extrachromosomal vector or a vector which is capable of integrating into the genome of a host cell. Appropriate vectors are well known in the art and described in Sambrook et al. (1998), Molecular Cloning, A Laboratory Manual, Cold Spring Harbor Press, and Ausubel et al. (1998), Current Protocols in Molecular Biology, John Wiley & Sons, for example.

The RNA molecule which is being expressed by the vector may be any RNA molecule having a length of from 15-500 nucleotides, preferably from 20-400 nucleotides. For example, the RNA may be a tRNA, an snRNA or a microRNA. Preferably, however, the RNA is an RNA molecule which is capable of RNA interference or an RNA molecule which is processed e.g. by cellular mechanisms to provide an RNA molecule which is capable of RNA interference. In an especially preferred embodiment, the RNA molecule is a single-stranded RNA molecule having a length of from 30-100, more preferably 40-80 nucleotides. The single-stranded RNA molecule has a portion which is at least substantially complementary to a target transcript, i.e. a transcript, particularly an mRNA which is expressed in a target cell. Further, it is preferred that the single-stranded RNA molecule is capable of forming a double-stranded hairpin structure. The hairpin structure preferably has a 3' overhang which may have a length from 1-5 nucleotides, more preferably from 1-3 nucleotides. In a further preferred embodiment, the RNA molecule is a double-stranded RNA molecule which is comprised of 2 single-stranded RNA molecules which are individually expressed by one or several vectors and which are capable of forming a double-stranded RNA molecule. The double-stranded RNA molecule comprises an antisense strand which is at least substantially complementary to a target transcript and a sense strand which is at least substantially complementary to the anti-sense strand. Each strand has a length from preferably 19-30, more preferably from 19-25 nucleotides. The double-stranded RNA molecule has preferably at least one 3' overhang which has a length from 1-5 nucleotides, more preferably from 1-3 nucleotides.

The expression control sequence comprises a polymerase III promoter, more particularly a polymerase III promoter which is recognised in a pre-determined host cell, e.g. a mammalian, particularly human, cell. Appropriate examples for polymerase III promoters are the H1 promoter, the U6 promoter, a tRNA promoter or other polymerase III promoters.

The expression control sequence may comprise one or several regulatory protein binding sites, e.g. 1, 2 or 3 regulatory protein-binding sites. Preferably at least one regulatory protein-binding site is located 5' to the TATA box of the polymerase III promoter. More preferably, at least one regulatory protein-binding site is located 5' and one regulatory protein-binding site is located 3' to the TATA box of the polymerase III promoter. The regulatory protein-binding site allows sequence specific binding of a regulatory protein and preferably has a length up to 25 nucleotides, more preferably up to 20 nucleotides.

The regulatory protein may be any protein which is capable of sequence-specific binding to a nucleic acid sequence, e.g. a repressor, a transcription factor, a nuclear receptor, etc. A preferred example of a regulatory protein is the tetracyline repressor, which is capable of sequence-specific binding to a short nucleic acid sequence. The binding of the tetracyline repressor to its binding site within the expression control sequence leads to a repression of transcription. The tetracycline repressor binding may be abolished by adding tetracyline or a derivative thereof, e.g. doxycycline to the culture medium, resulting in an induction of RNA expression. The regulatory protein which recognizes the binding site is capable of being expressed in a cell which has been transfected with the vector of the invention. The expression of the regulatory protein may be constitutive or regulatable. The regulatory protein may be a protein endogenous to the transfected cell or a protein exogenous to the transfected cell, i.e. a protein coded by a nucleic acid sequence which has been inserted into the cell by recombinant means. For example, the nucleic acid encoding the regulatory protein may be located on the vector of the invention where it is operatively linked to an appropriate expression control sequence.

Preferably, the expression control sequence further comprises a transcription terminator. The transcription terminator may be a naturally occurring terminator, e.g. the U6 or the H1 terminator or a synthetic terminator. Preferably, the terminator starts with a sequence of several T nucleotides.

The sequence of the RNA molecule encoded by the vector of the present invention has to have a sufficient complementarity to a nucleic acid target molecule in order to mediate target-specific RNA interference. More particularly, a portion of the RNA molecule is substantially complementary to the target transcript.

The target RNA cleavage reaction guided by the RNA molecules encoded by the vector of the present invention is highly sequence-specific. However, not all positions of the RNA molecule contribute equally to target recognition. Mismatches, particularly at the 3"-terminus of the RNA molecule, more particularly at the residues 3' to the first 20 nt of the RNA molecule are tolerated. Especially preferred are single-stranded RNA molecules or antisense strands of double-stranded RNA molecules having at the 5'-terminus at least 15 and preferably at least 20 nucleotides which are completely complementary to a predetermined target transcript or have only one mismatch and optionally up to 15 nucleotides at the 3"-terminus which may contain 1 or several, e.g. 2, 3 or more mismatches.

A further aspect of the present invention relates to a method of mediating RNA interference in a cell or an organism comprising the steps:
(a) contacting the cell or organism with the vector of the invention under conditions wherein target-specific nucleic acid modifications mediated by the RNA molecule encoded by the vector are repressed and
(b) inducing a target-specific nucleic acid modification effected by the vector-encoded RNA molecule towards a target nucleic acid having a sequence portion substantially complementary to the RNA molecule.

Preferably the contacting step (a) comprises introducing the vector into a target cell, e.g. an isolated target cell, e.g. in cell culture, a unicellular microorganism or a target cell or a plurality of target cells within a multicellular organism. More preferably, the introducing step comprises a carrier-mediated delivery, e.g. by liposomal carriers and/or by injection, or by delivery by electroporation, calcium phosphate precipitation, viral infection, etc. Further suitable delivery systems include Oligofectamine (Invitrogen) and Transit-TKO siRNA Transfection reagent (Mirus).

The method of the invention may be used for determining the function of a gene in a cell or an organism or even for modulating the function of a gene in a cell or an organism, being capable of mediating RNA interference. The cell is preferably a eukaryotic cell or a cell line, e.g. a plant cell or an animal cell, such as a mammalian cell, e.g. an embryonic cell, a pluripotent stem cell, a tumor cell, e.g. a teratocarcinoma cell or a virus-infected cell. The organism is preferably a eukaryotic organism, e.g. a plant or an animal, such as a mammal, particularly a human.

The target gene to which the RNA molecule is directed may be associated with a pathological condition. For example, the gene may be a pathogen-associated gene, e.g. a viral gene, a tumor-associated gene or an autoimmune disease-associated gene. The target gene may also be a heterologous gene expressed in a recombinant cell or a genetically altered organism. By determinating or modulating, particularly, inhibiting the function of such a gene valuable information and therapeutic benefits in the agricultural field or in the medicine or veterinary medicine field may be obtained.

The present invention also allows a highly specific targeting of transcripts in a cell or in an organism, e.g. the targeting of individual transcript isoforms or transcript polymorphisms.

The vector may be administered as a pharmaceutical composition. The administration may be carried out by known methods, wherein a nucleic acid is introduced into a desired target cell in vitro or in vivo. Commonly used gene transfer techniques include calcium phosphate, DEAE-dextran, electroporation and microinjection and viral methods (Graham, F. L. and van der Eb, A. J. (1973) Virol. 52, 456; McCutchan, J. H. and Pagano, J. S. (1968), J. Natl. Cancer Inst. 41, 351; Chu, G. et al (1987), Nucl. Acids Res. 15, 1311; Fraley, R. et al. (1980), J. Biol. Chem. 255, 10431; Capecchi, M. R. (1980), Cell 22, 479). A recent addition to this arsenal of techniques for the introduction of nucleic acids into cells is the use of cationic liposomes (Feigner, P. L. et al. (1987), Proc. Natl. Acad. Sci USA 84, 7413). Commercially available cationic lipid formulations are e.g. Tfx 50 (Promega) or Lipofectamin2000 (Life Technologies). A further preferred method for the introduction of nucleic acids into a target organism, particularly into a mouse, is the high-pressure tail vein injection (Lewis, D. L. et al. (2002), Nat. Genet. 29, 29; McCaffrey, A. P. et al. (2002), Nature 418, 38-39).

Thus, the invention also relates to a pharmaceutical composition containing as an active agent at least one vector as described above and pharmaceutically acceptable carriers, diluents and/or adjuvants. The composition may be used for diagnostic and for therapeutic applications in human medicine or in veterinary medicine.

For diagnostic or therapeutic applications, the composition may be in form of a solution, e.g. an injectable solution, a cream, ointment, tablet, suspension or the like. The composition may be administered in any suitable way, e.g. by injection, by oral, topical, nasal, rectal application etc. The carrier may be any suitable pharmaceutical carrier. Preferably, a carrier is used, which is capable of increasing the efficacy of the vector molecules to enter the target-cells. Suitable examples of such carriers are liposomes, particularly cationic liposomes. A further preferred administration method is injection.

A further preferred application of the RNAi method is a functional analysis of eukaryotic cells, or eukaryotic non-human organisms, preferably mammalian cells or organisms and most preferably human cells, e.g. cell lines such as HeLa or 293 or rodents, e.g. rats and mice. By transfection with vector molecules which are homologous to a predetermined target gene encoding a suitable RNA molecule, a specific knockout phenotype can be obtained in a target cell, e.g. in cell culture or in a target organism. The knockout phenotype may be regulated by induction or repression of the expression control sequence in the vector of the invention.

Further, the invention relates to a pharmaceutical composition for inhibiting the expression of a target transcript by RNA interference comprising as an active agent a vector as described above.

Furthermore, the invention relates to a method for the monitoring, prevention or treatment of a disease associated with overexpression of at least one target gene comprising administering a subject in need thereof a vector as described above.

Still a further subject matter of the present invention is a eukaryotic cell or a non-human transgenic animal which is transfected with a vector as described above. The cell may be a mammalian cell, e.g. a human cell. The non-human transgenic animal may be a mammal, e.g. a mouse, rat, hamster or monkey. The cell or animal may be transiently or stably tranfected. A stable transfection is preferred.

Further the invention relates to a clonal cell population derived from a cell as described above, wherein the clonal cell population substantially consists of transfected cells and is free from non-transfected cells.

The eukaryotic cell or eukaryotic non-human organism exhibits an inducible target gene-specific knockout phenotype comprising an at least partially deficient expression of at least one endogeneous target gene RNA. It should be noted that the present invention allows the simultaneous or subsequent transfection with several vectors coding for molecules of different sequences, which are either cognate to a different or the same target gene.

Gene-specific knockout phenotypes of cells or non-human organisms, particularly of human cells or non-human mammals may be used in analytic procedures, e.g. in the functional and/or phenotypical analysis of complex physiological processes such as analysis of gene expression profiles and/or proteomes. For example, one may prepare the knock-out phenotypes of human genes in cultured cells which are assumed to be regulators of alternative splicing processes. Among these genes are particularly the members of the SR splicing factor family, e.g. ASF/SF2, SC35, SRp20, SRp40 or SRp55. Further, the effect of SR proteins on the mRNA profiles of predetermined alternatively spliced genes such as CD44 may be analysed. Preferably the analysis is carried out by high-throughput methods using oligonucleotide based chips.

Using RNAi based knockout technologies, the expression of an endogeneous target gene may be inhibited in a target cell or a target organism. The endogeneous gene may be complemented by an exogeneous target nucleic acid coding for the target protein or a variant or mutated form of the target protein, e.g. a gene or a cDNA, which may optionally be fused to a further nucleic acid sequence encoding a detectable peptide or polypeptide, e.g. an affinity tag, particularly a multiple affinity tag. Variants or mutated forms of the target gene differ from the endogeneous target gene in that they encode a gene product which differs from the endogeneous gene product on the amino acid level by substitutions, insertions and/or deletions of single or multiple amino acids. The variants or mutated forms may have the same biological activity as the endogeneous target gene. On the other hand, the variant or mutated target gene may also have a biological activity, which differs from the biological activity of the endogeneous target gene, e.g. a partially deleted activity, a completely deleted activity, an enhanced activity etc.

The complementation may be accomplished by coexpressing the polypeptide encoded by the exogeneous nucleic acid, e.g. a fusion protein comprising the target protein and the affinity tag and the RNA molecule for knocking out the endogeneous gene in the target cell. This coexpression may be accomplished by using a suitable expression vector expressing both the polypeptide encoded by the exogeneous nucleic acid, e.g. the tag-modified target protein and the RNA molecule or alternatively by using a combination of expression vectors. Proteins and protein complexes which are synthesized de novo in the target cell will contain the exogeneous gene product, e.g. the modified fusion protein. In order to avoid suppression of the exogeneous gene product expression by the RNAi molecule, the nucleotide sequence encoding the exogeneous nucleic acid may be altered on the DNA level (with or without causing mutations on the amino acid level) in the part of the sequence which is homologous to the RNA molecule. Alternatively, the endogeneous target gene may be complemented by corresponding nucleotide sequences from other species, e.g. from mouse.

Preferred applications for the cell or organism of the invention is the analysis of gene expression profiles and/or proteomes. In an especially preferred embodiment an analysis of a variant or mutant form of one or several target proteins is carried out, wherein said variant or mutant forms are reintroduced into the cell or organism by an exogeneous target nucleic acid as described above. The combination of knockout of an endogeneous gene and rescue by using mutated, e.g. partially deleted exogeneous target has advantages compared to the use of a knockout cell. Further, this method is particularly suitable for identifying functional domains of the target protein. In a further preferred embodiment a comparison, e.g. of gene expression profiles and/or proteomes and/or phenotypic characteristics of at least two cells or organisms is carried out. These organisms are selected from:
(i) a control cell or control organism without target gene inhibition,
(ii) a cell or organism with target gene inhibition and
(iii) a cell or organism with target gene inhibition plus target gene complementation by an exogeneous target nucleic acid.

The method and cell of the invention may also be used in a procedure for identifying and/or characterizing pharmacological agents, e.g. identifying new pharmacological agents from a collection of test substances and/or characterizing mechanisms of action and/or side effects of known pharmacological agents.

Thus, the present invention also relates to a system for identifying and/or characterizing pharmacological agents acting on at least one target protein comprising:
(a) a eukaryotic cell or a eukaryotic non-human organism capable of expressing at least one endogeneous target gene coding for said target protein,
(b) at least one vector as described above encoding an RNA molecule capable of inhibiting the expression of said at least one endogeneous target gene by RNAi and
(c) a test substance or a collection of test substances wherein pharmacological properties of said test substance or said collection are to be identified and/or characterized.

Further, the system as described above preferably comprises:
(d) at least one exogeneous target nucleic acid coding for the target protein or a variant or mutated form of the target protein wherein said exogeneous target nucleic acid differs from the endogeneous target gene on the nucleic acid level such that the expression of the exogeneous target nucleic acid is substantially less inhibited by the RNA molecule than the expression of the endogeneous target gene.

Furthermore, the RNA knockout complementation method may be used for preparative purposes, e.g. for the affinity purification of proteins or protein complexes from eukaryotic cells, particularly mammalian cells and more particularly human cells. In this embodiment of the invention, the exogeneous target nucleic acid preferably codes for a target protein which is fused to an affinity tag.

The preparative method may be employed for the purification of high molecular weight protein complexes which preferably have a mass of 150 kD and more preferably of 500 kD and which optionally may contain nucleic acids such as RNA. Specific examples are the heterotrimeric protein complex consisting of the 20 kD, 60 kD and 90 kD proteins of the U4/U6 snRNP particle, the splicing factor SF3b from the 17S U2 snRNP consisting of 5 proteins having molecular weights of 14, 49, 120, 145 and 155 kD and the 25S U4/U6/U5 tri-snRNP particle containing the U4, U5 and U6 snRNA molecules and about 30 proteins, which has a molecular weight of about 1.7 MD.

Further, the present invention is explained in more detail in the following Figures and Examples.

EXAMPLES

1. Materials and Methods

1.1 Plasmid Construction

For plasmid construction of H1 promoter constructs, synthetic oligonucleotides were prepared and the hybridized and ligated to each other using T4 RNA ligase. The ligation product was then gel purified and ligated into the sequencing vector pBluescript SK(−) (Stratagene) that was restricted with XhoI and BamHI and gel-purified to remove the excised fragment of the multiple cloning site. To generate the H1-tetO4-insert, the following oligonucleotide strands were synthesized forming the sense orientation insert, 5'-TCGAA-GATCTAATATTTGCATGTCGCTATGTGT-TCTGGGAAATCACCATAAACGT G AAAT (SEQ ID NO: 1), 5'-pCCCTATCAGTGATAGAGACTTATAAGT-TCCCTATCAGTGATAGAGAATTCATTTC GAAGTAT-TCCGCGTACGTTTCGACG (SEQ ID NO:2), and 5'-pTACGCGGAATACTTC-GAAATTTTTCTCGAGCTTCCTTCGG-GAAGCTCTCCATAT TTTTTG (SEQ ID NO:3) were combined with the following oligonucleotides forming the antisense orientation insert, 5'-TATGGTGATTTCCCA-GAACACATAGCGACATGCAAATATTAGATCT (SEQ ID NO: 5'-pTACGCGGAATACTTCGAAATGAAT-TCTCTATCACTGATAGGGAACTTATAAGTCT CTAT-CACTGATAGGGATTTCACGTT (SEQ ID NO:5), and 5'-pGATCCAAAAAATATGGAGAGCTTC-CCGAAGGAAGCTCGAGAAAAAATTTCGAAG TAT-TCCGCGTACGTCGAAACG (SEQ ID NO:6). The XhoI site is no longer existent upon ligation of the H1 promoter insert; the BamH1 site remains intact. To insert a new hairpin sequence, the GL2 hairpin RNA sequence can be excised by digesting the plasmid with EcoRI and XhoI and ligating synthetic oligonucleotides, prehybridized to each other in that site.

1.2 Transfection and Knockdown Analysis

Per well of a 24 well plate, 1 μg pGL2-SV40 firefly luciferase plasmid, 0.2 μg pRL-TK seapansy luciferase plasmid, and 1 μg H1-promoter-hairpin plasmid were transfected using Lipofectamine 2000 (Invitrogen) according the manufacturers protocol. Doxycycline was used at a concentration of 0.2 μg/ml in the medium. The medium containing transfection reagent was replaced 8 h after transfection with fresh medium. Cells were harvested by trypsination and lysed according to the dual luciferase kit instructions (Promega). Luciferase activity was monitored thereafter. If cells were first primed with H1-hairpin-plasmids, 2 μg of plasmid DNA was used for transfection. The medium containing transfection reagent was replaced 8 h after transfection with fresh medium, and transfection was repeated with the mixture of reporter and H1 plasmids as described.

2. Results

We constructed a total of five H1-derived promoters to drive transcription of a stem-loop RNA structure directed against the firefly luciferase GL2. All contain the same proximal sequence element, PSE, and the same transcription terminator. The presumed transcription start is the first nucleotide of the stem-loop as listed below. The presumed termination is about two to four nucleotides within the first run of 6 thymidines of the terminator portion.

The region around the TATA box is variable: in H1, it is derived from the 'proper' H1 promoter. H1-tetO1, H1-tetO2, and H1-tetO2 each contain one binding site for the tetracyclinee repressor tetR. H1-tetO4 contains two tetR-binding sites.

To check the effect of these constructs in vivo, we transiently co-transfected the plasmids containing the H1 cassette with two reporter plasmids encoding the luciferase GL2 and the *Renilla* luciferase. The plasmid encoding the GL2 luciferase exhibits sequence homology to the expressed stem-loop; its expression should be suppressed by the stem-loop. The plasmid encoding the seapansy (*Renilla* luciferase (pRL-TK), in contrast, exhibits no sequence homology and is not affected. Therefore, we calculated the ratio of the GL2 luciferase activity over the *Renilla* luciferase activity (the two enzymes can be distinguished as they use different substrates). The ratio obtained in the presence of an empty vector instead of the H1 cassette was arbitrarily set to 1. Thus, a ratio of less than 1 indicates reduced expression of the GL2 luciferase and hence suppression of the gene. In this study, we used 'T-Rex' HeLa cells (Invitrogen) that constitutively express the tetR protein. We anticipated that the H1-tetO constructs are fully active only in the presence of the tetracycline analogue doxycycline (dox) when the tetR protein does not bind its responsive element on the DNA. Note that the luciferase activities vary slightly in the presence or absence of doxycycline. Therefore, the respective controls were independently set to 1. The luciferase activities were assayed two days after transfection to allow for full expression of the repressing stem-loop. After three days, the absolute activities were greatly diminished due to the transient nature of the transfection, but the ratios are largely the same.

Figure 1:
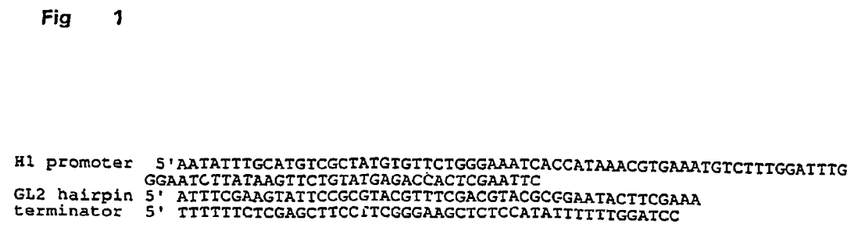
FIG. 1. Sequences of the unmodified H1 promoter sequence (SEQ ID NO:7) including the GL2 hairpin sequence (SEQ ID NO:8) and the terminator sequences (SEQ ID NO:9) for polymerase III. The sequences are seamlessly joined to each other in the plasmid.
Figure 2:
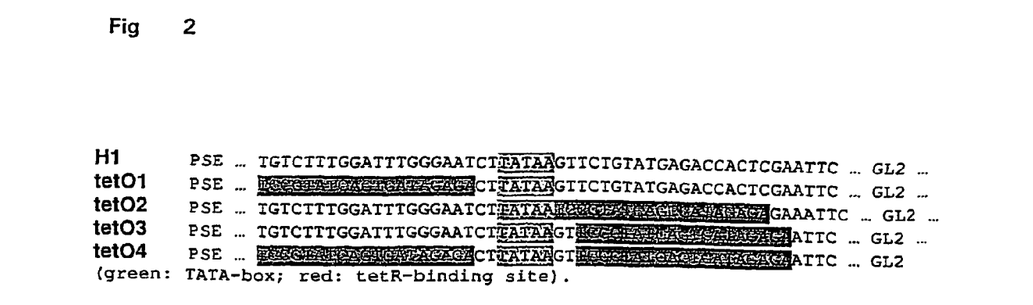
FIG. 2. Illustration of the position of tetO binding sites (tetO1-SEQ ID NO:11; tetO2-SEQ ID NO:12; tetO3-SEQ ID NO:13; tetO4-SEQ ID NO: 14) inserted into the H1 promoter region (SEQ ID NO:10). Transcription would begin immediately downstream of the 3'-most nucleotide shown. Preferably, the first transcribed nucleotide encodes a purine nucleotide.
Figure 3:
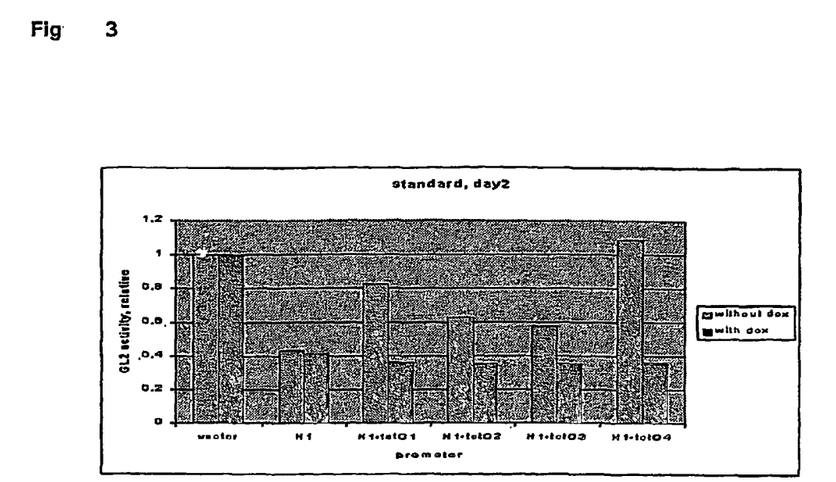
FIG. 3. Targeting of GL2 luciferase with hairpin expression vectors directed against GL2.

As shown in the FIG. 3, co-transfection of the H1 cassette reduces the GL2 activity to 40% of the control, irrespective of the presence or absence of doxycycline. Similar values are obtained for all H1-tetO constructs in the presence of doxycycline, i.e., in the absence of tetR binding. In the absence of doxycycline, however, tetR can bind to the H1 promoter, and the constructs are less active: H1-tetO1 reduces the GL2 activity to 0.82, H1-tetO2 to 0.62, and H1-tetO3 to 0.58. Thus, the tet repressor appears to suppress transcription of the stem-loop more efficiently when bound upstream of the TATA box as compared to downstream. The most drastic effect was observed for the construct that contains two tetR-binding sites: in the presence of doxycycline, this cassette represses GL2 luciferase expression as well as the other constructs. In the absence of doxycycline, however, the GL2 luciferase activity is apparently even increased, to 1.09. The increase is probably within the experimental error and thus not significant, but GL2 activity is certainly not decreased. Therefore, the H1 promoter containing two tetR binding sites is inactive in the absence of doxycycline, and thus suitable for regulated suppression of a target gene.

In this experiment, none of the constructs reduced GL2 luciferase activity to less than 0.4, thus leaving a significant background of expressed luciferase. We believe that this background does not result from a general inability of the stem-loop to suppress the luciferase. Instead, we think that transcription of the stem-loop and maturation into a functional RISC complex takes longer than the expression of active luciferase, thus leaving a significant background of luciferase expressed in the absence of silencing stem-loops. Additionally, the ratio of plasmids introduced into individual cells may differ, i.e., one cell may obtain more of the H1 plasmid, and another less. Those cells that did not obtain enough of the repressing plasmid may have contributed to the background activity. In support of these notions, prolonged expression (up to three days after transfection) led to a decreased 'background level' of GL2 activity: in this experiment, 0.26 to 0.33 (data not shown).

Figure 4:
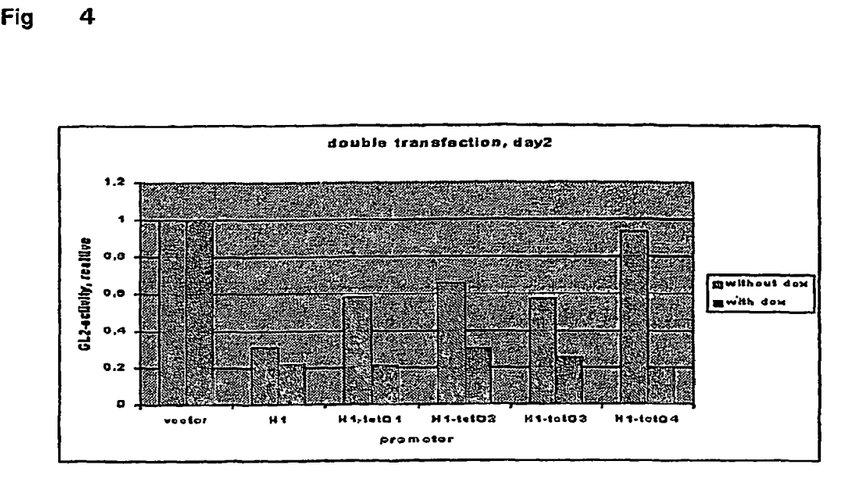
FIG. 4. Targeting of GL2 luciferase with hairpin expression vectors directed against GL2. The H1 promoter hairpin constructs were transfected a day prior to reporter plasmid transfection to allow for expression of hairpin RNA prior to expression of reporter plasmids.
Figure 5:
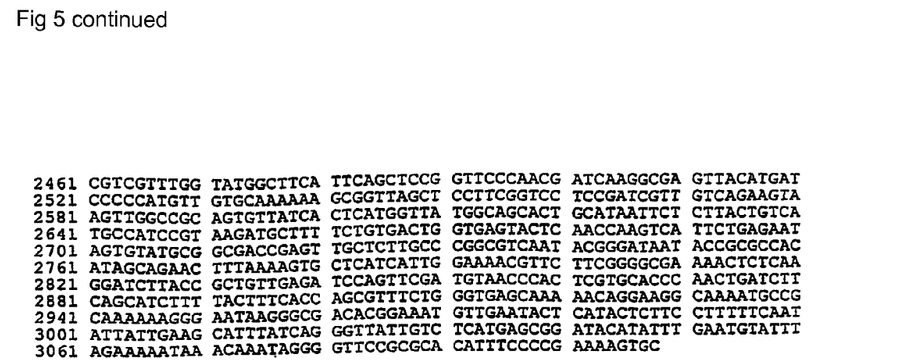
FIG. 5. The nucleic acid sequence of the plasmid pH1-tet04 (SEQ ID NO:15) used for inducible silencing of GL2 luciferase.

More importantly, transfection of the H1 cassettes only, followed by co-transfection of the two luciferases plus the H1 cassette one day later increases the effect of the stem-loop expression (FIG. 4): in this set of experiments, the GL2 activities in the presence of doxycycline ranged between 20 and 30% of the control. As before, the H1-tetO4 construct has, in the absence of doxycycline, the same effect as H1 without tetR binding sites, whereas in the presence of doxycycline it is not significantly active (0.94).

As silencing hairpin, a 23 base pair stem was selected, whereby the stem-loop of the sequence UUCG was connected to the 3' end of the antisense strand complementary to the GL2 target mRNA. The terminator signal was positioned such that a 2 to 4 nucleotide oligoU 3'-overhang would be present on the transcribed hairpin. The loop sequence may also be exchanged with a six-nucleotide sequence of a restriction enzyme, allowing linearization of the plasmid prior to sequencing. Sequencing of hairpin RNAs is sometimes cumbersome because of the stable hairpin structure through that can prevent the sequencing polymerase from reading through. Stems of 19 base pairs or greater (up to 29 base pairs) can be used in hairpin-mediated gene silencing.

3. Summary

In conclusion, the H1 cassette described here is capable of reducing expression of a target gene, and the variant H1-tetO4 allows for full control of the repression by addition of doxycycline to the medium. To demonstrate that the construct can fully suppress a given target gene, it is preferred to establish permanent a cell line that is either insensitive to the transfection of GL2 luciferase or that does not express an endogenous protein. The (endogenous) protein can be switched on and off by doxycycline when using the H1-tetO4 variant. That in particular would pave the way to switch off essential genes in a reliable and reproducible way.

The expression cassette, when integrated in the context of a selectable plasmid backbone, can be stably integrated into mammalian cells. Mammalian cells also stably expressing tetR protein can then be induced to express the hairpin RNA. Essential genes can than be turned off in cells at any given time upon the addition of doxycycline to the tissue culture medium. Homogenous knockdown cell populations can be obtained overcoming problems of inhomogeneous transfection. These cell lines will be of high value for proteomic or gene profile type analysis. An inducible promoter/hairpin system may also be used in transgenic animals to generate gene knockdowns (rather than gene knockouts) by feeding tetracycline or doxycycline. This may be useful for generating animal models of disease that are caused by reduction of endogenous gene expression.

REFERENCES

Barton G. M., and Medzhitov R. 2002. Retroviral delivery of small interfering RNA into primary cells. Proc. Natl. Acad. Sci. USA 99: 14943-14945.

Bitko V., and Bark S. 2001. Phenotypic silencing of cytoplasmic genes using sequence-specific double-stranded short interfering RNA and its application in the reverse genetics of wild type negative-strand RNA viruses. BMC Microbiol. 1: 34.

Brummelkamp T., Bernards R., and Agami R. 2002a. Stable suppression of tumorigenicity by virus-mediated RNA interference. Cancer Cell 2: 243.

Brummelkamp T. R., Bernards R., and Agami R. 2002b. A system for stable expression of short interfering RNAs in mammalian cells. Science 296: 550-553.

Devroe E., and Silver P. A. 2002. Retrovirus-delivered siRNA. BMC Biotechnol 2: 15.

Elbashir S. M., Lendeckel W., and Tuschl T. 2001a. RNA interference is mediated by 21 and 22 nt RNAs. Genes & Dev. 15: 188-200.

Elbashir S. M., Harborth J., Lendeckel W., Yalcin A., Weber K., and Tuschl T. 2001b. Duplexes of 21-nucleotide RNAs mediate RNA interference in mammalian cell culture. Nature 411: 494-498.

Elbashir S. M., Martinez J., Patkaniowska A., Lendeckel W., and Tuschl T. 2001c. Functional anatomy of siRNAs for mediating efficient RNAi in Drosophila melanogaster embryo lysate. EMBO J. 20: 6877-6888.

Elbashir S. M., Harborth J., Weber K., and Tuschl T. 2002. Analysis of gene function in somatic mammalian cells using small interfering RNAs. Methods 26: 199-213.

Hutvágner G., and Zamore P. D. 2002. A microRNA in a multiple-turnover RNAi enzyme complex. Science 1: 1.

Lagos-Quintana M., Rauhut R., Lendeckel W., and Tuschl T. 2001. Identification of novel genes coding for small expressed RNAs. Science 294: 853-858.

Lagos-Quintana M., Rauhut R., Yalcin A., Meyer J., Lendeckel W., and Tuschl T. 2002. Identification of tissue-specific microRNAs from mouse. Curr. Biol. 12: 735-739.

Lau N. C., Lim L. P., Weinstein E. G., and Bartel D. P. 2001. An abundant class of tiny RNAs with probable regulatory roles in Caenorhabditis elegans. Science 294: 858-862.

Lee N. S., Dohjima T., Bauer G., Li H., Li M. J., Ehsani A., Salvaterra P., and Rossi J. 2002. Expression of small interfering RNAs targeted against HIV-1 rev transcripts in human cells. Nat. Biotech. 20: 500-505.

Lee R. C., and Ambros V. 2001. An extensive class of small RNAs in Caenorhabditis elegans. Science 294: 862-864.

Llave C., Xie Z., Kasschau K. D., and Carrington J. C. 2002. Cleavage of Scarecrow-like mRNA targets directed by a class of Arabidopsis miRNA. Science 297: 2053-2056.

Martinez J., Patkaniowska A., Urlaub H., Luhrmann R., and Tuschl T. 2002. Single-stranded antisense siRNAs guide target RNA cleavage in RNAi. Cell 110: 563-574.

McManus M. T., and Sharp P. A. 2002. Gene silencing in mammals by small interfering RNAs. Nat. Rev. Genet. 3: 737-747.

McManus M. T., Petersen C. P., Haines B. B., Chen J., and Sharp P. A. 2002. Gene silencing using micro-RNA designed hairpins. RNA 8: 842-850.

Miyagishi M., and Taira K. 2002. U6 promoter driven siRNAs with four uridine 3' overhangs efficiently suppress targeted gene expression in mammalian cells. Nat. Biotech. 20: 497-500.

Mourelatos Z., Dostie J., Paushkin S., Sharma A., Charroux B., Abel L., Rappsilber J., Mann M., and Dreyfuss G. 2002. miRNPs: a novel class of ribonucleoproteins containing numerous microRNAs. Genes & Dev. 16: 720-728.

Myslinski E., Amé J.-C., Krol A., and Carbon P. 2001. An unusually compact external promoter for RNA polymerase III transcription of the human H1 RNA gene. Nucleic Acids Res. 29: 2502-2509.

Ohkawa J., and Taira K. 2000. Control of the functional activity of an antisense RNA by a tetracycline-responsive derivative of the human U6 snRNA promoter. Hum. Gene Ther. 11: 577-585.

Paddison P. J., and Hannon G. J. 2002. RNA interference: the new somatic cell genetics? Cancer Cell 2: 17-23.

Paul C. P., Good P. D., Winer I., and Engelke D. R. 2002. Effective expression of small interfering RNA in human cells. Nat. Biotech. 20: 505-508.

Paule M. R., and White R. J. 2000. Transcription by RNA polymerase I and III. Nucleic Acids Res. 28: 1283-1298.

Rhoades M., Reinhart B., Lim L., Burge C., Bartel B., and Bartel D. 2002. Prediction of plant microRNA targets. Cell 110: 513.

Tuschl T., and Borkhardt A. 2002. Small interfering RNAs—a revolutionary tool for analysis of gene function and gene therapy. Mol. Intervent. 2: 42-51.

Xia H., Mao Q., Paulson H. L., and Davidson B. L. 2002. siRNA-mediated gene silencing in vitro and in vivo. Nat. Biotech. 20: 1006-1010.

Zeng Y., Wagner E. J., and Cullen B. R. 2002. Both natural and designed micro RNAs can inhibit the expression of cognate mRNAs when expressed in human cells. Mol. Cell 9: 1327-1333.

The invention claimed is:

1. A method for inhibiting target gene expression in vitro, comprising administering to a cell, a recombinant vector for the regulatable expression of a single-stranded or double-stranded RNA molecule in a eukaryotic cell comprising at least one sequence coding for the RNA molecule operatively linked to an expression control sequence comprising a polymerase III promoter and at least two repressor protein-binding sites, wherein at least one repressor protein-binding site is located 5' and at least a second repressor binding site is located 3' to the TATA box of the promoter.

2. A method for inhibiting target gene expression in vivo, comprising administering to a cell, a recombinant vector for the regulatable expression of a single-stranded or double-stranded RNA molecule in a eukaryotic cell comprising at least one sequence coding for the RNA molecule operatively linked to an expression control sequence comprising a polymerase III promoter and at least two repressor protein-binding sites, wherein at least one repressor protein-binding site is located 5' and at least a second repressor binding site is located 3' to the TATA box of the promoter.

3. A method for monitoring a disease comprising administering a pharmaceutical composition comprising at least one recombinant vector for the regulatable expression of a single-stranded or double-stranded RNA molecule in a eukaryotic cell comprising at least one sequence coding for the RNA molecule operatively linked to an expression control sequence comprising a polymerase III promoter and at least two repressor protein-binding sites, wherein at least one repressor protein-binding site is located 5' and at least a second repressor binding site is located 3' to the TATA box of the promoter as an active ingredient and pharmaceutically acceptable carriers, diluents and/or adjuvants, to a patient in need of such monitoring, and determining expression of said RNA molecule as an indication of the progress of said disease.

4. The method according to claim 3, wherein the monitored disease is associated with overexpression of at least one target manuscript.

5. A method for a treating a disease associated with overexpression of at least one target manuscript, comprising administering to a patient a therapeutic amount of a pharmaceutical composition comprising at least one vector RNA molecule comprising at least one sequence coding for the RNA molecule operatively linked to an expression control sequence comprising a polymerase III promoter and at least two repressor protein-binding sites, wherein at least one repressor protein-binding site is located 5' and at least a second repressor binding site is located 3' to the TATA box of the promoter, wherein the patient is in need of treatment of a disease associated with overexpression of at least one target manuscript.

6. The method of claim 5, wherein the disease associated with overexpression of at least one target manuscript is selected from the group consisting of tumor diseases, inflammatory diseases, infectious diseases, degenerative diseases and autoimmune diseases.

7. A non-human transgenic animal which is transfected with a recombinant vector for the regulatable expression of a single-stranded or double-stranded RNA molecule in a eukaryotic cell comprising at least one sequence coding for the RNA molecule operatively linked to an expression control sequence comprising a polymerase III promoter and at least two repressor protein-binding sites, wherein at least one repressor protein-binding site is located 5' and at least a second repressor binding site is located 3' to the TATA box of the promoter.

8. The non-human animal of claim 7, wherein said animal is a mammal.

* * * * *

SEQUENCE LISTING

```
<160> NUMBER OF SEQ ID NOS: 15

<210> SEQ ID NO 1
<211> LENGTH: 60
```

```
<212> TYPE: DNA
<213> ORGANISM: Artificial sequence
<220> FEATURE:
<223> OTHER INFORMATION: oligonucleotide primer with homology to
      prokaryotic or eukaryotic sequence

<400> SEQUENCE: 1
tcgaagatct aatatttgca tgtcgctatg tgttctggga atcaccata aacgtgaaat    60

<210> SEQ ID NO 2
<211> LENGTH: 80
<212> TYPE: DNA
<213> ORGANISM: Artificial sequence
<220> FEATURE:
<223> OTHER INFORMATION: oligonucleotide primer with homology to
      prokaryotic or eukaryotic sequence
<220> FEATURE:
<221> NAME/KEY: misc_feature
<222> LOCATION: (1)..(1)
<223> OTHER INFORMATION: phosphorylated

<400> SEQUENCE: 2
ccctatcagt gatagagact tataagttcc ctatcagtga tagagaattc atttcgaagt    60
attccgcgta cgtttcgacg                                                80

<210> SEQ ID NO 3
<211> LENGTH: 61
<212> TYPE: DNA
<213> ORGANISM: Artificial sequence
<220> FEATURE:
<223> OTHER INFORMATION: oligonucleotide primer with homology to
      prokaryotic or eukaryotic sequence
<220> FEATURE:
<221> NAME/KEY: misc_feature
<222> LOCATION: (1)..(1)
<223> OTHER INFORMATION: phosphorylated

<400> SEQUENCE: 3
tacgcggaat acttcgaaat tttttctcga gcttccttcg ggaagctctc catatttttt    60
g                                                                    61

<210> SEQ ID NO 4
<211> LENGTH: 46
<212> TYPE: DNA
<213> ORGANISM: Artificial sequence
<220> FEATURE:
<223> OTHER INFORMATION: oligonucleotide primer with homology to
      prokaryotic or eukaryotic sequence

<400> SEQUENCE: 4
tatggtgatt cccagaaca catagcgaca tgcaaatatt agatct                    46

<210> SEQ ID NO 5
<211> LENGTH: 80
<212> TYPE: DNA
<213> ORGANISM: Artificial sequence
<220> FEATURE:
<223> OTHER INFORMATION: oligonucleotide primer with homology to
      prokaryotic or eukaryotic sequence
<220> FEATURE:
<221> NAME/KEY: misc_feature
<222> LOCATION: (1)..(1)
<223> OTHER INFORMATION: phosphorylated

<400> SEQUENCE: 5
tacgcggaat acttcgaaat gaattctcta tcactgatag ggaacttata agtctctatc    60
actgataggg atttcacgtt                                                80
```

```
<210> SEQ ID NO 6
<211> LENGTH: 75
<212> TYPE: DNA
<213> ORGANISM: Artificial sequence
<220> FEATURE:
<223> OTHER INFORMATION: oligonucleotide primer with homology to
      prokaryotic or eukaryotic sequence
<220> FEATURE:
<221> NAME/KEY: misc_feature
<222> LOCATION: (1)..(1)
<223> OTHER INFORMATION: phosphorylated

<400> SEQUENCE: 6
gatccaaaaa atatggagag cttcccgaag gaagctcgag aaaaaatttc gaagtattcc      60
gcgtacgtcg aaacg                                                      75

<210> SEQ ID NO 7
<211> LENGTH: 100
<212> TYPE: DNA
<213> ORGANISM: Artificial sequence
<220> FEATURE:
<223> OTHER INFORMATION: polymerase III promoter recognized by mammalian
      cell

<400> SEQUENCE: 7
aatatttgca tgtcgctatg tgttctggga aatcaccata aacgtgaaat gtctttggat      60
ttgggaatct tataagttct gtatgagacc actcgaattc                           100

<210> SEQ ID NO 8
<211> LENGTH: 49
<212> TYPE: DNA
<213> ORGANISM: Firefly luciferase

<400> SEQUENCE: 8
atttcgaagt attccgcgta cgtttcgacg tacgcggaat acttcgaaa                  49

<210> SEQ ID NO 9
<211> LENGTH: 47
<212> TYPE: DNA
<213> ORGANISM: Artificial sequence
<220> FEATURE:
<223> OTHER INFORMATION: polymerase III transcription terminator
      recognized by mammalian cell

<400> SEQUENCE: 9 tttttctcg agcttccttc gggaagctct ccatattttt tggatcc                    47

<210> SEQ ID NO 10
<211> LENGTH: 51
<212> TYPE: DNA
<213> ORGANISM: Artificial sequence
<220> FEATURE:
<223> OTHER INFORMATION: polymerase III promoter recognized by mammalian
      cell
<220> FEATURE:
<221> NAME/KEY: misc_feature
<222> LOCATION: (22)..(26)
<223> OTHER INFORMATION: TATA box

<400> SEQUENCE: 10
tgtctttgga tttgggaatc ttataagttc tgtatgagac cactcgaatt c               51

<210> SEQ ID NO 11
<211> LENGTH: 51
<212> TYPE: DNA
<213> ORGANISM: Artificial sequence
<220> FEATURE:
```

```
<223> OTHER INFORMATION: prokaryotic
<220> FEATURE:
<221> NAME/KEY: misc_feature
<222> LOCATION: (1)..(19)
<223> OTHER INFORMATION: tetR-binding site
<220> FEATURE:
<221> NAME/KEY: misc_feature
<222> LOCATION: (22)..(26)
<223> OTHER INFORMATION: TATA box

<400> SEQUENCE: 11
tccctatcag tgatagagac ttataagttc tgtatgagac cactcgaatt c        51

<210> SEQ ID NO 12
<211> LENGTH: 52
<212> TYPE: DNA
<213> ORGANISM: Artificial sequence
<220> FEATURE:
<223> OTHER INFORMATION: prokaryotic
<220> FEATURE:
<221> NAME/KEY: misc_feature
<222> LOCATION: (22)..(26)
<223> OTHER INFORMATION: TATA box
<220> FEATURE:
<221> NAME/KEY: misc_feature
<222> LOCATION: (27)..(45)
<223> OTHER INFORMATION: tetR-binding site

<400> SEQUENCE: 12
tgtctttgga tttgggaatc ttataatccc tatcagtgat agagagaaat tc       52

<210> SEQ ID NO 13
<211> LENGTH: 51
<212> TYPE: DNA
<213> ORGANISM: Artificial sequence
<220> FEATURE:
<223> OTHER INFORMATION: prokaryotic
<220> FEATURE:
<221> NAME/KEY: misc_feature
<222> LOCATION: (22)..(26)
<223> OTHER INFORMATION: TATA box
<220> FEATURE:
<221> NAME/KEY: misc_feature
<222> LOCATION: (29)..(47)
<223> OTHER INFORMATION: tetR-binding site

<400> SEQUENCE: 13
tgtctttgga tttgggaatc ttataagttc cctatcagtg atagagaatt c        51

<210> SEQ ID NO 14
<211> LENGTH: 51
<212> TYPE: DNA
<213> ORGANISM: Artificial sequence
<220> FEATURE:
<223> OTHER INFORMATION: prokaryotic
<220> FEATURE:
<221> NAME/KEY: misc_feature
<222> LOCATION: (1)..(19)
<223> OTHER INFORMATION: tetR-binding site
<220> FEATURE:
<221> NAME/KEY: misc_feature
<222> LOCATION: (22)..(26)
<223> OTHER INFORMATION: TATA box
<220> FEATURE:
<221> NAME/KEY: misc_feature
<222> LOCATION: (29)..(47)
<223> OTHER INFORMATION: tetR-binding site

<400> SEQUENCE: 14
tccctatcag tgatagagac ttataagttc cctatcagtg atagagaatt c        51

<210> SEQ ID NO 15
```

<211> LENGTH: 3108
<212> TYPE: DNA
<213> ORGANISM: Artificial sequence
<220> FEATURE:
<223> OTHER INFORMATION: synthetic expression vector containing prokaryotic and eukaryotic sequences

<400> SEQUENCE: 15

```
cacctgacgc gccctgtagc ggcgcattaa gcgcggcggg tgtggtggtt acgcgcagcg      60
tgaccgctac acttgccagc gccctagcgc ccgctccttt cgctttcttc ccttcctttc     120
tcgccacgtt cgccggcttt ccccgtcaag ctctaaatcg ggggctccct ttagggttcc     180
gatttagtgc tttacggcac ctcgacccca aaaaacttga ttagggtgat ggttcacgta     240
gtgggccatc gccctgatag acggtttttc gccctttgac gttggagtcc acgttcttta     300
atagtggact cttgttccaa actggaacaa cactcaaccc tatctcggtc tattcttttg     360
atttataagg gattttgccg atttcggcct attggttaaa aaatgagctg atttaacaaa     420
aatttaacgc gaattttaac aaaatattaa cgcttacaat ttccattcgc cattcaggct     480
gcgcaactgt tgggaagggc gatcggtgcg ggcctcttcg ctattacgcc agctggcgaa     540
agggggatgt gctgcaaggc gattaagttg ggtaacgcca gggttttccc agtcacgacg     600
ttgtaaaacg acggccagtg aattgtaata cgactcacta tagggcgaat gggtaccgg      660
gccccccctc gaagatctaa tatttgcatg tcgctatgtg ttctgggaaa tcaccataaa     720
cgtgaaatcc ctatcagtga tagagactta aagttccct atcagtgata gagaattcat      780
ttcgaagtat tccgcgtacg tttcgacgta cgcggaatac ttcgaaattt tttctcgagc     840
ttccttcggg aagctctcca tattttttgg atccactagt tctagagcgg ccgccaccgc     900
ggtggagctc cagcttttgt tccctttagt gagggttaat ttcgagcttg gcgtaatcat     960
ggtcatagct gtttcctgtg tgaaattgtt atccgctcac aattccacac aacatacgag    1020
ccggaagcat aaagtgtaaa gcctggggtg cctaatgagt gagctaactc acattaattg    1080
cgttgcgctc actgcccgct ttccagtcgg gaaacctgtc gtgccagctg cattaatgaa    1140
tcggccaacg cgcggggaga ggcggtttgc gtattgggcg ctcttccgct tcctcgctca    1200
ctgactcgct gcgctcggtc gttcggctgc ggcgagcggt atcagctcac tcaaaggcgg    1260
taatacggtt atccacagaa tcaggggata acgcaggaaa gaacatgtga gcaaaaggcc    1320
agcaaaaggc caggaaccgt aaaaaggccg cgttgctggc gtttttccat aggctccgcc    1380
ccccctgacga gcatcacaaa aatcgacgct caagtcagag gtggcgaaac ccgacaggac    1440
tataaagata ccaggcgttt ccccctggaa gctccctcgt gcgctctcct gttccgaccc    1500
tgccgcttac cggatacctg tccgcctttc tcccttcggg aagcgtggcg ctttctcata    1560
gctcacgctg taggtatctc agttcggtgt aggtcgttcg ctccaagctg ggctgtgtgc    1620
acgaaccccc cgttcagccc gaccgctgcg ccttatccgg taactatcgt cttgagtcca    1680
acccggtaag acacgactta tcgccactgg cagcagccac tggtaacagg attagcagag    1740
cgaggtatgt aggcggtgct acagagttct tgaagtggtg gcctaactac ggctacacta    1800
gaaggacagt atttggtatc tgcgctctgc tgaagccagt taccttcgga aaaagagttg    1860
gtagctcttg atccggcaaa caaaccaccg ctggtagcgg tggtttttt gtttgcaagc    1920
agcagattac gcgcagaaaa aaaggatctc aagaagatcc tttgatcttt tctacggggt    1980
ctgacgctca gtggaacgaa aactcacgtt aagggatttt ggtcatgaga ttatcaaaaa    2040
ggatcttcac ctagatcctt ttaaattaaa aatgaagttt taaatcaatc taagtatat      2100
atgagtaaac ttggtctgac agttaccaat gcttaatcag tgaggcacct atctcagcga    2160
```

-continued

```
tctgtctatt tcgttcatcc atagttgcct gactccccgt cgtgtagata actacgatac      2220
gggagggctt accatctggc cccagtgctg caatgatacc gcgagaccca cgctcaccgg      2280
ctccagattt atcagcaata aaccagccag ccggaagggc cgagcgcaga agtggtcctg      2340
caactttatc cgcctccatc cagtctatta attgttgccg ggaagctaga gtaagtagtt     2400
cgccagttaa tagtttgcgc aacgttgttg ccattgctac aggcatcgtg gtgtcacgct     2460
cgtcgtttgg tatggcttca ttcagctccg gttcccaacg atcaaggcga gttacatgat     2520 ccccatgtt  gtgcaaaaaa gcggttagct ccttcggtcc tccgatcgtt gtcagaagta     2580
agttggccgc agtgttatca ctcatggtta tggcagcact gcataattct cttactgtca     2640
tgccatccgt aagatgcttt tctgtgactg gtgagtactc aaccaagtca ttctgagaat     2700
agtgtatgcg gcgaccgagt tgctcttgcc cggcgtcaat acgggataat accgcgccac     2760
atagcagaac tttaaaagtg ctcatcattg gaaaacgttc ttcggggcga aaactctcaa     2820
ggatcttacc gctgttgaga tccagttcga tgtaacccac tcgtgcaccc aactgatctt     2880
cagcatcttt tactttcacc agcgtttctg ggtgagcaaa aacaggaagg caaaatgccg     2940 caaaaaggg  aataagggcg acacggaaat gttgaatact catactcttc cttttcaat     3000 attattgaag catttatcag ggttattgtc tcatgagcgg atacatattt gaatgtattt     3060
agaaaaataa acaaataggg gttccgcgca catttccccg aaaagtgc                  3108
```